United States Patent [19]
Bichon et al.

[11] Patent Number: 4,766,160

[45] Date of Patent: Aug. 23, 1988

[54] PHOTO-HARDENABLE COMPOSITION FOR BIOACTIVE COATINGS

[75] Inventors: Daniel Bichon, Gaillard; Van Tao Nguyen, Cruseilles, both of France; Michel Schneider, Troinex, Switzerland

[73] Assignee: Battelle Memorial Institute, Carouge, Switzerland

[21] Appl. No.: 887,627

[22] Filed: Jul. 21, 1986

[30] Foreign Application Priority Data

Jul. 22, 1985 [CH] Switzerland ............... 03164/85

[51] Int. Cl.$^4$ ............................................. C08J 3/28
[52] U.S. Cl. ..................................... 522/46; 435/180; 435/181; 522/175; 427/54.1
[58] Field of Search ............... 522/175, 46; 435/180, 435/182; 427/54.1

[56] References Cited

U.S. PATENT DOCUMENTS

| | | | |
|---|---|---|---|
| 4,192,727 | 3/1980 | Ward | 522/175 |
| 4,297,185 | 10/1981 | Chevreux et al. | 522/96 |
| 4,451,568 | 5/1984 | Schneider et al. | 435/181 |

*Primary Examiner*—Allan M. Lieberman
*Attorney, Agent, or Firm*—Cushman, Darby & Cushman

[57] ABSTRACT

A hydrophilic coating photopolymerizable in air, capable of fixing bioactive molecules is formed from a mixture of acrylic or methacrylic monomers containing at least 20% by weight of an approximately quimolecular mixture of acrylic acid and an N-dialkylated aminoalcohol acrylate or methacrylate.

5 Claims, 1 Drawing Sheet

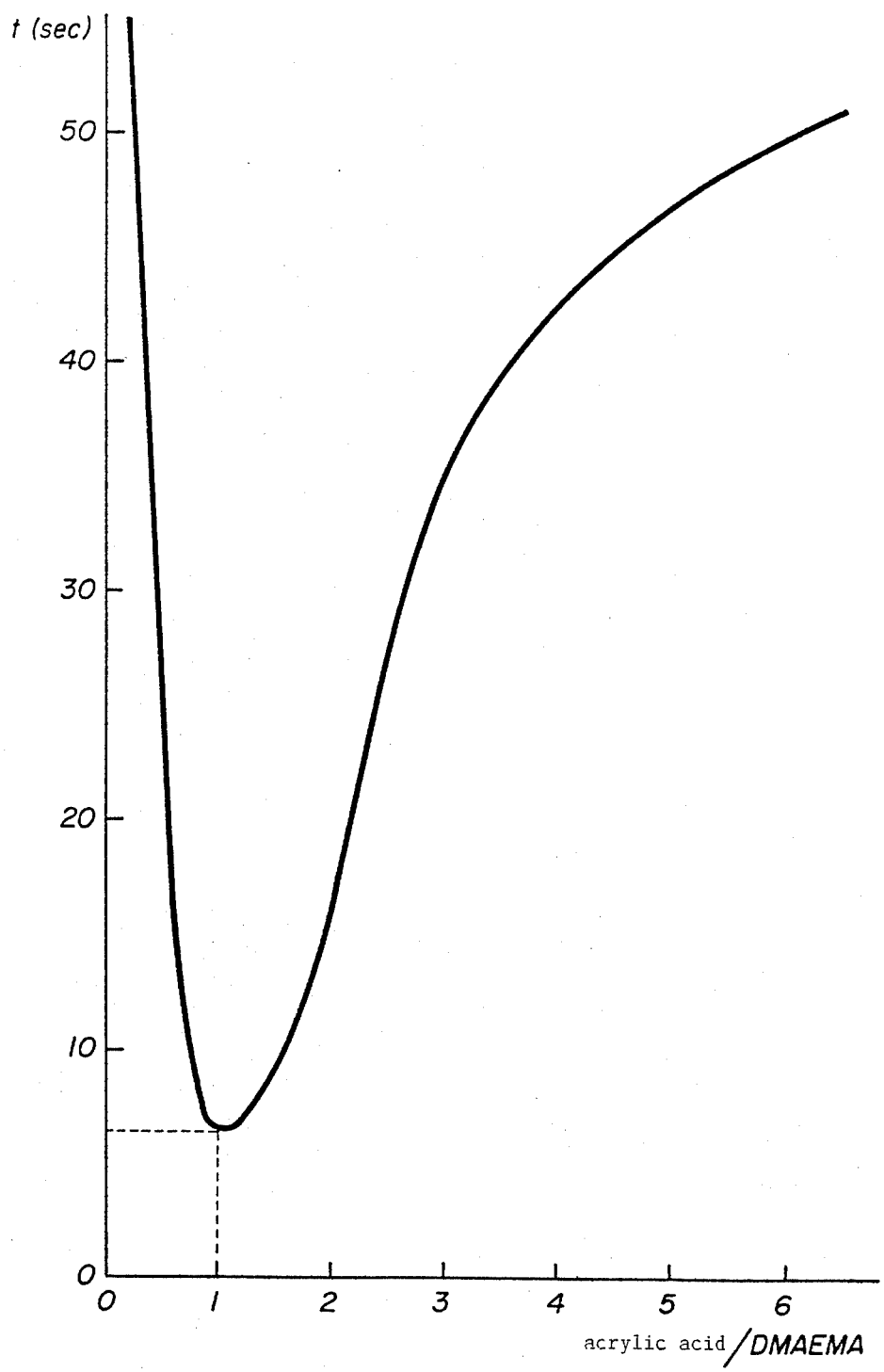

PHOTO-HARDENABLE COMPOSITION FOR BIOACTIVE COATINGS

The invention relates to coatings used as supports for bioactive substances. The term "bioactive" refers to substances playing a part in interactions of biological nature, i.e. processes involving the reacting of substance such as ferments, enzymes, enzyme inhibitors, hormones, antigens, antibodies, heparin, lectins etc. "Supports" refers to the media, generally applied to substrates used in biological methods which are capable, by any means, of retaining bioactive substances so that they can be used in biological processes.

U.S. Pat. No. 4,451,568, explains in detail the meaning of "bioactive substances" (whether the activity is direct or indirect) and describes a number of known supports of use in binding bioactive substances, and methods of doing so (see also P. L. KNONICK, Synthetic Biomedical Polymers, Technomic Publication, Westports, Mass USA (1982) page 153). The patent also describes (and indeed discloses) an adhesive photopolymerisable composition which, when applied to substrates, provides coatings which are adhesive even in the presence of water and which can advantageously be used as supports for immobilising bioactive substances. A coating of this kind, after photo-hardening, provides a resin support which is hydrophilic though insoluble in water and combines with aqueous solutions to form a hydrogel permeable to bioactive substances. The resin contains copolymerised structural elements capable of covalently bonding the bioactive molecules with which one is concerned and consequently of retaining them permanently. The great advantage of this technique over the prior art is to provide supports on a wide variety of substrates (glass, metals, plastic and others), the supports being firmly adhesive and having a thickness which can easily be controlled (by varying the viscosity of the photopolymerisable mixture and the application parameters) and can be hardened by irradiation in a very short time.

This photo-hardenable composition is based on: acrylic acid (A) (between 10 and 70% by weight of the composition), an amino-alcohol acrylate or methacrylate (B) as a polymerisation activator and adhesion promoter (0.5 to 15%) one or more monomers copolymerisable with acrylic acid and possessing groups capable of fixing bioactive substances (up to 50% by weight) and a photoinitiator acting as a hydrogen abstractor (see e.g. C G RAFFEY: Photopolymerisation of Surface Coating, John Wyley & Sons (1982), Page 85), notably benzophenone or derivatives thereof (0.5–10% by weight). This composition gives excellent results provided it is protected from atmospheric oxygen during polymerisation. This is because oxygen acts as a poymerisation inhibitor and the aforementioned compositions harden badly, if at all, in the presence of oxygen. An attempt has therefore been made to eliminate this disadvantage and to this end, in the photopolymerisable composition, the proportions of acrylic acid (A) and amino-alcohol ester (B) have been kept in the immediate neighbourhood of the equimolecular ratio 1:1 (with a tolerance of about 5–10%): a composition containing components (A) and (B) in these proportions will rapidly photopolymerise in air. It has also been found that if the photopolymerised coating is to remain sufficiently hydrophilic, the composition must contain at least 20 to 25% by weight of the aforementioned equimolecular mixture.

More specifically, therefore, one object of the invention is a composition photo-hardenable in air and adapted to provide on substrates coatings which are adhesive even in the presence of water, the coatings being formed from a resin which is hydrophilic but insoluble in water and which forms a hydrogel capable of immobilising bioactive substances. The composition contains at least 20% by weight of a first photopolymerisable ingredient (I), up to 70% by weight of a second photopolymerisable ingredient (II), 0.5 to 10% of a photosensitiser (III) and, optionally, one or more other co-photopolymerisable ingredients (IV) to be defined hereafter, in sufficient quantity to make up 100%: The ingredient I consists of an approximately equimolecular mixture (1:1) of acid (A) and an acrylic or methacrylic ester of a tertiary hydroxyalkyldialkylated amine (B), components (A) and (B) being present in mixture I partly in the form of a covalent combination (A-B) which gradually forms by reaction between A and B and partly in the form of an amine acrylate, i.e. the corresponding ammonium salt $(A^-xBH^+)$. The covalent composition A-B is a carboxybetaine having the following formula:

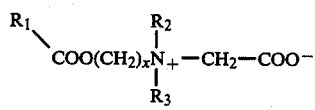

where $R_1 =$ H or $CH_3$, $\alpha = 1$ to 5 and $R_2$ and $R_3 = CH_3$, $C_2H_5$, alkyl.

Formation of carboxybetaines of this kind is known per se and has been described in the literature—see e.g. the following references:

A. Le Berre et A. Delacroix. Bulletin de la Societe Chimique de France vol. 2 page 647 (1973) and volume 7-8 page 2404 (1973) and also U.S. Pat. No. 3,671,502.

Carboxybetaines form spontaneously when acrylic acid is mixed with the tertiary acrylic base.

The chemical reactions which occur are as follows:

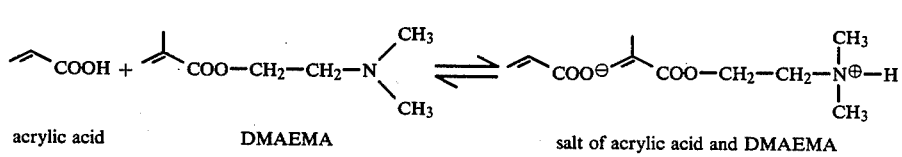

acrylic acid      DMAEMA      salt of acrylic acid and DMAEMA

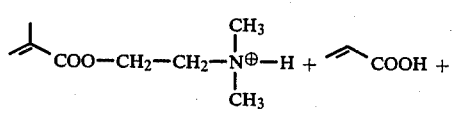

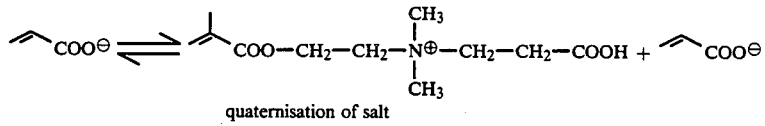

quaternisation of salt

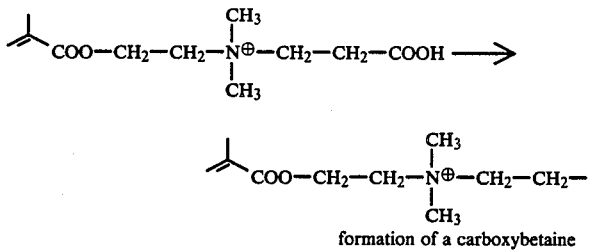

formation of a carboxybetaine

In this mixture, the proportion of carboxybetaine to salt is variable but approaches 35% after storage for a few days. (The proportion can be determined by titrating the residual tertiary amine in the mixture). Prolonged storage of the mixture may result in the formation of carboxybetaine crystals; this should be avoided since it makes it more difficult to apply the mixture.

It should be noted that in U.S. Pat. No. 4,297,185, a similar covalent combination is used (i.e. a betaine obtained by addition of one mol of acrylic acid to one mol of tertiary amine) in an adhesive polymerisable composition. However, the adhesive prescribed in this document was used for manufacturing laminated panels by sticking and, after setting, must be resistant to swelling by moisture, i.e. precisely the opposite behaviour from the product according to the invention. Also, the adhesive photopolymerises only after being sheltered from air by pressing between the panels to be stuck together. In addition its composition includes a relatively large excess of one or other of the components A and B as compared with the equimolar ratio which we have seen, is impossible according to the present invention.

The references on related subjects also include the document U.S. Pat. No. 4,167,464, which discloses photopolymerisable compositions containing acrylic acid salts and alkyl acrylates in the form of films and filaments. These photopolymerised substances are used as porous members for absorption of water.

Ingredient II is represented by one or more copolymerisable monomers bearing groups adapted to fix bioactive molecules subsequently when the coating is photopolymerised. In general these substances are acrylic derivatives having the formula $CH_2=CH-COR$ where R represents the following group phenoxy (or orthiophenoxy) which may or may not be substituted by one or more electrophilic substituents such as Cl, Br, CN, COOEt, trialkylammonium, $NO_2$, $SO_3H$, sulphamido. OH, $SO_2CH_3$,

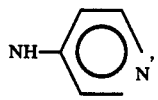

phenylazo; heterocylic groups such as 1-phenyl-3-methyl-5-pyrazolyl, N-phthalimido, N-succinimido, N-glutarimido, N-ethoxycarbonyl-amido, N-perchlorobenzoylamido, N-benzoylamido, trimethylacetylamido, N-(2-pyridinyl), N-benzo-triazolyl, N-dihydrobenzotriazinonyl, N-piperidyl; vinyl groups substituted in position 2, such as $-CH=C(CN)Ph$;

N-imino groups such as $-N=C(CN)COOEt$ and alkyl or cycloalkyl groups bearing oxirane or isocyanato groups. The corresponding methacrylic compounds are less suitable since they are less reactive during photopolymerisation. The aforementioned monomers all have a group capable of reacting, for example, with an amine grouping of a bioactive molecule to be captured. Other compounds containing such functional groups (acylating agents, protective groups, compounds bearing "leaving groups") are abundantly described in the literature on peptide synthesis. A considerable proportion of these olefinic monomers comprising the aforementioned functional groups are of use in the invention provided they can be photopolymerised. The following compounds are examples: N-hydroxysuccinimide acrylate, N-hydroxysuccinimide acrylamido-caproate, epoxypropanol acrylate, 2-hydroxyethyl acrylate and 2-isocyanato-ethyl acrylate. Other examples of these compounds are cited in German patent application DE-A-2 237 083. Oxirane monomers and isocyanates are particularly preferred since they also become bonded to the OH groups of the substances to be immobilised and they do not liberate splittable groups.

The photosensitiser and polymerisatin photoinitiator III can be chosen from most of the substances generally known as such and compatible with the monomers in the composition. The following substances may be cited as examples: benzophenone, Mischler ketone, 4-dimethylaminoethyl benzoate, benzil, 2-ethylanthraquinone, diethoxyacetophenone, UVECRYL P-36 (Union Chimique Belge), IRGACURE-651 ET-184 (Ciba), SANDORY-1000 (Sandoz), FI-4 (Eastman Kodak), VICURE-10 and -30 (Stauffer Chemicals), TRIGONAL-14 and -P- (Noury Chemicals), DAROCURE-1173 and -1116 (Merck), and 2-chlorothioxanthone. Most of the photoinitiators identified above by their commercial names are derivatives of benzophenone. Some, such as P-36 are olefin derivatives of benzophenone and copolymerise with the other monomers. In general, quantities of the order of 1 to 2% by weight of photoinitiator in the present composition are sufficient.

The following are examples of other copolymerisable monomers (IV) which can if required be added to the present composition: acrylamide, dimethylacrylamide, and other olefin monomers such as acrylic and methacrylic esters, polyfunctional acrylates and acrylic prepolymers. Monofunctional acrylic esters can be added to obtain more binder and a more adequately viscous adhesive composition and also to adjust the hygrophilicity of the copolymer after photo-hardening. The amounts of these adjuvants should therefore be varied by the skilled addressee as needed, depending on the properties to be given to the intended copolymer. The following are examples of esters which can be used: lower alkyl acrylate methacrylates, (methyl, ethyl, propyl, butyl, isobutyl, tert, butyl, etc.,) docecyl, diethylhexyl, methoxyethyl, etc. Polyfunctional acrylates can be used to give greater rigidity to the copolymer as needed. The following are examples: trimethylolpropane triacrylate (TMPTA), pentaerythritol triacrylate (PETRA), and the corresponding tetraacrylate, (PETEA). The acrylic or vinyl prepolymers can be added in small quantities to the composition according to the invention when it is desired to increase its flexibility and elasticity. Examples of such prepolymers are the compounds known commercially as UVITHANE (THIOKOL Corporation), and EBECRYL (Union Chimique Belge). Similar prepolymers are described in British patent specification No. 1,430,422 and German patent application DOS No. 2 542 314.

The techniques used to prepare the present composition, the method of using if for coating substrates and the use of these substrates for fixing bioactive substances are identical with those described in document EP-A-29 411. Consequently, reference to the document should be made with regard to the general detailed operation thereof, apart from variant compositions specific to the present invention and illustrated in the following examples.

BRIEF DESCRIPTION OF THE DRAWINGS

The accompanying drawing graphically shows the irradiation time necessary for hardening a photopolymerisable composition in air depending on the molar ratio between acrylic acid and DMAEMA.

EXAMPLE 1

The following constituents were intimately mixed in a laboratory vessel: 10 g (1 equivalent) acrylic acid, 22 g (1.01 equivalent) dimethylaminoethyl methacrylate (DMAEMA), 20 g dimethylacrylamide, 40 g 2-hydroethyl acrylate and 1 g UVECRYL P-36 photoinitiator. An approximately 50–100 μm film of this mixture (viscosity approximately 300 cP at 25° C.) was spread on a glass plate and irradiated in air by a UV lamp supplying 30 W/cm at a distance of 30 cm. Hardening occurred in about 30 seconds at ambient temperature. The film was then used to fix heparin via a connecting bridge consisting of butylene diisocyanate in identical manner with the technique described in example 3 of document EP-A-29 411.

By way of comparison, a composition was prepared under similar conditions but the weight ratio 10:22 between acrylic acid and DMAEMA was replaced by a ratio 26:6 between the same ingredients. Photopolymerisation tests on a film having this composition showed that no hardening occurred in air after five minutes of irradiation, whereas under nitrogen the film solidified in 20–30 seconds.

EXAMPLE 2

A series of compositions were prepared containing 50% of a mixture of acrylic acid and DMAEMA, 5% of UVECRYL P-36 photoinitiator, 30% 2-hydroxyethyl acrylate and 15% dimethylacrylamide. The molar ratio between acrylic acid and DMAEMA varied between 1:2 and 5:1 in the series of samples. A photo-hardening test in air was made on each sample, spread in the form of a thin film on a glass plate. In these tests, the constant deciding criterion was the formation of a thin film which did not stick to the finger. In practice, of course, the irradiation times will be longer in order completely to solidify the film. The results obtained are shown in the following table, where the relative proportions of acrylic acid and DMAEMA (molar ratio) are shown in relation to the irradiation time in air necessary for the indicated degree of polymerization.

| Equiv. of Acrylic Acid mol Equiv. of DMAEMA mol | Irridiation Time (sec) |
| --- | --- |
| 0.5 | 20 |
| 1 | 8 |
| 1.5 | 10 |
| 2 | 18 |
| 2.5 | 28 |
| 3 | 36 |
| 5 | 47 |

The above results clearly show that hardening the air is more efficient when the acrylic acid-DMAEMA molar ratio is near unity.

EXAMPLE 3

A composition was prepared containing 5 g (1 equivalent) of acrylic acid, 10.9 g DMAEMA (1 equivalent), 10 g dimethylacrylamide, 3 g of N-hydroxysuccinimide acrylamido-caproate (NACHHS) and 1.5 g of UVECRYL P-36.

After two minutes irradiation in air as in Example 1, this composition gave resistant films which were insoluble in water but swelled therein without coming away from the substrates (nylon or PVC) on which they had been deposited.

The film was used to fix bioactive molecules as follows:

A coating having the above composition applied to a glass plate was converted into a film about 20 μm thick by irradiation at ambient temperature for two minutes under a 30 W/cm UV lamp. The film was immersed in a solution of albumin tagged with iodine 125 (50 mg/ml in a 0.1M, pH6 PBS buffer). After incubation at 22° C., the film was washed in plenty of twice-distilled water, dried, and its albumin-fixing power was determined by measuring the radioactivity associated with the sample. It was found that the fixation rate was 100 μg/cm$^2$. By comparison a film similar in every respect but not containing NACNHS when mixed, could fix only 0.2 μg of albumin/cm$^2$ under the same conditions (i.e. by simple absorption).

Although the films are made from a substance insoluble in water, they absorb water and swell until they practically double in weight and volume. Because of their hydrophilic nature under these conditions, their capacity to fix biomolecules is remarkably high (since the molecules can penetrate in the film by diffusion and are not only fixed at its outer surface).

There hydrogels, in coating or other forms, have very numerous biomedical applications, notably in the following sectors: sutures, catheters, IUDs (intra-uterine devices) detoxification of blood, probes for electrodes, vascular transplants, cellular culture substrates, biocompatible materials, contact lenses etc.

Composite products formed from a hydrophobic solid substrate and a hydrogel can combine the rigidity of the support with the properties of the hydrogel.

EXAMPLE 4

The various formulations hereafter were obtained by using an equimolecular mixture of acrylic acid (AA) and DMAEMA.

Each of these composition gave coating which were photopolymerisable in air and of use for fixing biomolecules by the method described in Example 3.

| Ingredients (Parts by Weight) | Composition | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Mixture of AA and DMAEMA | 56 | 71 | 60 | 60 | 30 | 84 | 34 | 74 | 44 | 49 | 64 | 34 |
| Glycidyl acrylate* | — | — | 17 | 34 | 64 | 10 | 60 | 20 | 50 | 30 | 30 | 30 |
| NACNHS** | 20 | 15 | 17 | — | — | — | — | — | — | — | — | — |
| Phenoxyethyl acrylate | 20 | 10 | — | — | — | — | — | — | — | 15 | 0 | 30 |
| TPGDA*** | 1 | 1 | 1 | 1 | 1 | 1 | 1 | 1 | 1 | 1 | 1 | 1 |
| P 36 | 3 | 3 | 5 | 5 | 5 | 5 | 5 | 5 | 5 | 5 | 5 | 5 |
| | 0 | | | | | | | | | | | |

*$CH_2=CH-COO-CH2-CH-CH2$
**N—hydroxysuccinimide N—acrylyl-6-aminocaproate
***tripropylene glycol diacrylate

We claim:

1. In a photopolymerisable composition which when irradiated in air gives a hydrophilic resin which swells in water but is insoluble therein, the resin being of use as such or in the form of a film-producing coating adhering firmly to the surface of a substrate such as glass, ceramic, plastics or metals, for immobilizing and fixing bioactive substances to the surface of the film or in the mass of the resin, the composition comprising:
    (i) at least 20% by weight of a first photopolymerisable ingredient (I) consisting of acrylic acid (A) and an acrylate or methacrylate of an N-dialkylated aminoalcohol (B);
    (ii) 5 to 70% by weight of a second photopolymersiable ingredient (II) consisting of one or more olefinic monomers copolymerisable with components A and B and bearing reactive groups capable of bonding to the bioactive molecules to be fixed;
    (iii) 0.5 to 10% of a photoinitiator or polymerization photosensitizer (III) compatible with the monomers herein;
    wherein the improvement comprises the molar ratio between components A and B is between 0.9 and 1.1, and that components A and B are present in the mixture partly in the form of an amine acrylate and partly in the form of a carboxybetaine addition reaction product of A and B; and wherein the proportion of carboxybetaine to amine acrylate is up to 35%;
    wherein the recited component percentages are in sufficient quantity to make up 100%.

2. The composition of claim 1, wherein the photoinitiator is a benzophenone derivative copolymerisable with the other monomers.

3. The composition of claim 1 further comprising a photopolymerizable ingredient (IV) comprising one or more copolymerizable monomers selected from acrylic and methacrylic esters, substituted and non-substituted acrylamide and mono-, di- and polyfunctional acrylic prepolymers, in sufficient quantity to make up 100%.

4. A method of preparing a film-producing coating for immobilizing bioactive substances on substrates, said method, comprising:
    irradiating a photopolymerizable composition, in air, for about 10 to about 120 seconds in a UV flux of 30 W/cm; and
    forming a film of a thickness of from about 10 to about 200μ;
    wherein said film is hydrophilic and swells in water but is insoluble therein and wherein said film is capable of immobilizing and fixing bioactive substances;
    wherein said photopolymerizable composition is one comprising;
    (i) at least 20% by weight of a first photopolymerisable ingredient (I) consisting of acrylic acid (A) and an acrylate or methacrylate of an N-dialkylated, amino-alcohol (B);
    (ii) 5 to 70% by weight of a second photopolymerisable ingredient (II) consisting of one or more olefinic monomers copolymerisable with components A and B and bearing reactive groups capable of bonding to the bioactive molecules to be fixed;
    (iii) 0.5 to 10% of photoinitiator or polymerization photosensitizer (III); and
    wherein the molar ratio between components A and B is between 0.9 and 1.1 and components A and B are present in the mixture partly in the form of an amine acrylate and partly in the form of a carboxybetaine addition reaction product of A and B wherein the portion of carboxybetaine to amine acrylate is up to 35%;
    wherein the recited component percentages are in sufficient quantity to make up 100%.

5. The method of claim 4 wherein the photopolymerizable composition further comprises a photopolymerizable ingredient (iv) comprising one or more copolymerizable monomers selected from acrylic and methacryllic esters, substituted and non-substituted acrylamide and mono-, di- and polyfunctional acrylic prepolymers in sufficient quantity to make up 100%.

* * * * *